United States Patent [19]

Li

[11] Patent Number: 5,710,293

[45] Date of Patent: Jan. 20, 1998

[54] METHOD OF PREPARATION OF ESTER DERIVATIVES OF STEROIDS

[75] Inventor: Fang Li, New York, N.Y.

[73] Assignee: The Population Council, Center for Biomedical Research, New York, N.Y.

[21] Appl. No.: 542,664

[22] Filed: Oct. 13, 1995

[51] Int. Cl.$^6$ .................................................. C07J 75/00
[52] U.S. Cl. .................. 552/595; 552/559; 552/560; 552/561; 552/562; 552/563; 552/564; 552/565; 552/566; 552/567; 552/570; 552/571; 552/572; 552/573; 552/574; 552/575; 552/577; 552/580; 552/581; 552/592; 552/593; 552/594
[58] Field of Search .................. 552/559, 560, 552/561, 562, 563, 564, 565, 566, 567, 570, 571, 572, 573, 574, 575, 577, 580, 581, 592, 593, 594, 595

[56] References Cited

U.S. PATENT DOCUMENTS

| 4,224,320 | 9/1980 | Dahl et al. |
|---|---|---|
| 5,223,492 | 6/1993 | Nasraoui et al. |

FOREIGN PATENT DOCUMENTS

| 1091660 | 11/1967 | United Kingdom .......... C07C 169/02 |

OTHER PUBLICATIONS

Kasal, et al, Collect Czech Chem Commun, vol. 53, pp. 619–628 (1993).

J. Org. Chem. –(1956), vol. 1, 21 pp. 240–241, E. Batres, (Miss) Rosario Gomez, G. Rosenkranz & Franz Sondheimer –"Steroids. LXXVI. Synthesis of Long Chain Carboxylic Acid Esters 17α–Hydroxyprogesterone".

Journal of Medicinal Chemistry, (1972), vol. 15, No. 7, E.L. Shapiro, L. Weber, H. Harris, C. Miskowicz, R. Neri, and H.L. Heroz –"Synthesis and Biological Activity of 17–Esters of 6–Dehydro–16–methylene–17–α–hydroxyprogesterones".

Wissenschaftliche Laboratorien des VEB Jenapharm, Jena, Pharmazie 30, H.1 (1975) –U. Eberhardt –"Steroide aus Hyodesoxycholsaure".

Chem. Ber. –102, pp. 643–658 (1969) –Werner, Mehrhof, Klaus Irmscher, Rolf Erb, und Ludwig Pohl –Synthesewege zum 17α–Hydroxy–16–methylen–19–nor–progesteron und seinen Derivaten.

Tetrahedren Letters, No. 20, pp. 1925–1929 –(1967), Pergamen Press Ltd. V. Schwarz, J. Zachova and K. Syhora –"Steroid Derivatives L. (1) A Synthesis of 16–Methylene–17α–Acetoxy–19–NOR–Progesterone".

Chemical Abstract, –Copyright 1995 ACS.

International Search Report mailed Aug. 6, 1996.

Primary Examiner—Kimberly J. Prior
Attorney, Agent, or Firm—Lerner, David, Littenberg, Krumholz & Mentlik

[57] ABSTRACT

The present invention relates to a method of using a perchloric acid catalyzed reaction to make acyl derivatives of norprogesterone compounds and, in particular, 16-methylene-17α-hydroxy-19-norpregn-4-ene-3,20-dione.

22 Claims, No Drawings

METHOD OF PREPARATION OF ESTER DERIVATIVES OF STEROIDS

The United States Government provided funding for this invention through Cooperative Agreements No. DPE-3050-A-00-8059-00 from the U.S. Agency for International Development. Therefore, the United States Government may have limited rights in this patent application.

FIELD OF THE INVENTION

The present invention relates to methods of forming ester derivatives of certain steroids and, in particular, converting certain steroid based norprogesterone alcohols, to the corresponding ester derivatives.

BACKGROUND OF THE INVENTION

The acid-catalyzed condensation of alcohols to esters has been known for some time. For example, the acid-catalyzed condensation of an alcohol with a carboxylic acid is known to yield an ester and water. This is generally known as a Fischer esterification reaction. It is a reversible process and the equilibrium lies slightly to the side of the production of the products when the reactants are simple alcohols and carboxylic acids. When the reaction is used for preparative purposes, the position of the equilibrium can be made more favorable by using either the alcohol or the carboxylic acid in excess. For example, methanol (0.6 mol.) plus benzoic acid (0.1 mol.) can be reacted to form methyl benzoate (isolated in 70% yield based on benzoic acid) and water. The reaction requires the addition of heat and sulfuric acid as a catalyst. The use of other acids such as, hydrochloric acid and trifluoro acetic acid are also known.

Esters may also be formed by the reaction of alcohols with acyl halides such as an acyl chloride. This yields the ester plus hydrogen chloride. These reactions are normally carried out in the presence of a weak base such as pyridine. Pyridine not only captures the hydrogen chloride that is formed but also exerts a catalytic effect.

Another closely related class of reactions involves carboxylic acid anhydrides which react similarly to acyl halides. Thus for example, 2-phenylethanol plus trifluoroacetic anhydride can be reacted to produce 2-phenylethyl trifluoroacetate and trifluoroacetic acid when the reaction is conducted in the presence of pyridine.

In general, these same types of reactions are useful for converting alcohol groups on a tetracyclic ring system characterizing steroids. See Shapiro et al., "Synthesis and Biological Activity at 17-Esters of 6-Dehydro-16-methylene-17α-hydroxyprogesterone", *Journal of Medicinal Chemistry*, (1972) 15, 716–720; and Batres et al., "Steroids. LXXVI. Synthesis of Long Chain Carboxylic Acid Esters—17α-Hydroxyprogesterone", *J. Org. Chem.*, (1956), 21, 240–41. However, when attempting to produce compounds like NESTORONE™ progestin, (16-methylene-17α-acetoxy-19-norpregn-4-ene-3,20-dione), unexpected difficulties were encountered. Specifically, norprogestins, because of the absence of a methyl group in position 19, are more twisted then their progesterone counterparts. This provides a significant increase in steric hindrance around the 17α position. In addition, the presence of the exomethylene group in position 16 provides an additional source of reactivity and additional steric hindrance in the same area. For those reasons, some difficulty in producing esters in the 17α position could have been expected. However, the usual methods of acylation, including reactions using pyridine, acyl halides and anhydrides failed, were unsatisfactory. Thus, while there are other esterification methods which can be used generally, the inventors have found that those methods are not generally useful derivatives for acylating 16-methylene-17α-hydroxy-19-norpregn-4-ene-3,20-dione. See Mehrhof, Irmsher, Erb, and Pohl, "Synthesewege Zum 17α-hydroxy-16-methylen-19-norprogresteron und Seinen Derivaten", *Chem. Ber* (1969), 102, 643–658 and Schwarze, Zachova and Syhora "Steroid Derivatives L(1). A Synthesis of 16-methylene-17α-acetoxy-19-nor-progesterone", *Tetrahedron Letters*, (1967), 20, 1925–1929. This particular subclass of steroids has been found by the inventors to be extremely difficult to acylate in the 17α position.

SUMMARY OF THE INVENTION

It has been discovered that steroid compounds known as norprogestins having a tetracyclic ring system substituted in the 16th position with an exomethylene or a functionally similar group, and having a hydroxyl group in the 17α position can be conveniently and efficiently acylated by the use of acylating agents such as anhydrides, acyl halides and the like, so long as the proper acid catalyst is used. The inventors have found that perchloric acid works efficiently and effectively to provide relatively high yields of the acyl derivatives of the norprogestins in question while other acids that should have been expected to work, yielded little or no reaction at all, an undesirable level of side products, or both. In particular, the present invention relates to a method of synthesizing acylated derivatives of steroids comprising the steps of: providing a norprogesterone compound having the tetracyclic ring system of asteroid substituted in at least the 16th position with an exomethylene or similar group and at the 17α position with a hydroxyl group; and reacting the norprogestin compound with at least one acylating compound in the presence of perchloric acid, so as to form a reaction mixture containing the corresponding acyl derivative of the steroid compound. The method is particularly useful for converting compounds based on a 16-methylene-17α-hydroxy-19-norpregn-4-ene-3,20-dione, and its related compounds, to the 17α-acyl derivatives thereof.

In particularly preferred embodiments in accordance with the present invention the methods of synthesizing acylated derivatives of 16-methylene-17α-hydroxy-19-norpregn-4-ene-3,20-dione include the step of providing a 16-methylene-17α-hydroxy-19-norpregn-4-ene-3,20-dione dissolved in a solvent. This compound is then reacted with at least a stoichiometric amount of at least one acylating compound selected from the group consisting of an anhydride and an acyl halide in the presence of perchloric acid in an amount of between about 0.1 to 5 times the stoichiometric amount of norprogesterone so as to form the corresponding acyl derivative thereof. The practice of the present invention can, in certain embodiments, lead to reactions conducted at room temperature with high yield and relatively few by-products. Such processes are a significant advance in terms of efficacy, efficiency and cost. Energy costs may be minimized, separation and extraction costs are kept low and the reaction can be run efficiently in a single reactive step.

DETAILED DESCRIPTION OF THE PREFERRED EMBODIMENT

As used herein, asteroid compound having the tetracylic ring system of a steroid means a compound having a ring structure of Formula (I):

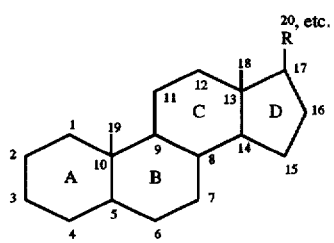

Formula (I)

Compounds falling within the class known as steroids include cholesterol, vitamin $D_3$, bile acids, corticosteroids and sex hormones such as testosterone, estradiol and progesterone as well as synthetic substances such as norprogesterone. The latter class of compounds are important in that many of its members, including the acylate derivatives, are superior to progesterone when taken orally to inhibit ovulation thereby inducing temporary infertility. The resulting oral contraceptives are widely used today. See Francis A. Carey "ORGANIC CHEMISTRY", McGraw Hill Book Company, 1987, Pages 575–578 and 1070–1076, the text of which is hereby incorporated by reference. Thus the term steroid compound in accordance with the present invention includes derivatives and substitutions of the basic tetracyclic ring which is common to the class. In particular, steroid compounds in accordance with the present invention are those which include certain specific substitutions. For example, the steroids should have, at least, an exomethylene or functionally similar group in the 16th position and the hydroxyl group in the 17α position. They should also be norprogesterones having an H instead of $CH_3$ in the 19th position. One such compound, 16-methylene-17α-hydroxy-19-norprogesterone (Compound 1, R═H), is illustrated in Formula II.

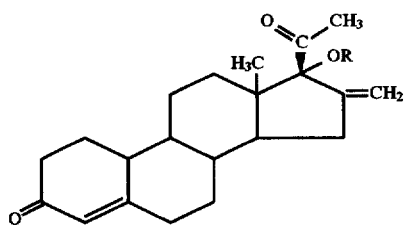

Formula (II)

| R = H | 1 |
| R = —COCH₃ | Nestorone ™ |
| R = —COCH₂CH₃ | 2 |
| R = —COCH₂CH₂CH₃ | 3 |
| R = —COCH₂CH₂CH₂CH₃ | 4 |
| R = —COCH₂CH₂CH₂CH₂CH₃ | 5 |

When the inventors set out to acylate the 17α-hydroxy-norprogesterone, they anticipated some difficulties relative to the analogous progesterone compound. The inventors knew that the absence of the methyl group in position 19, which distinguishes norprogesterone from progesterone, often creates difficulties in trying to make certain substitutions elsewhere on the steroid molecule. This coupled with the fact that the molecule already had a methylene group in the 16th position, gave them cause for additional concern. Therefore, instead of initially trying gentler and more conventional techniques such as the use of sulfuric or hydrochloric acid, the inventors employed an acid catalytic reaction using TsOH in an attempt to overcome the anticipated difficulties. However, they discovered, notwithstanding these steps, that the yield was still modest (20 to 30%) and the resulting mixture of compounds made separation, extraction and isolation very difficult.

Of course, not all substituents on the steroid backbone will have an effect on the chemistry of the 17α position. In terms of the present invention, so long as such substitutions or deletions would not significantly alter the reactivity of the 17α group i.e. will not render it more or less reactive, they are considered to be within the scope of the invention. For example, certain substitutions can be made at the 2nd, 4th, 6th or 11th position such as by introduction of a halide, methyl or methylene group and such substitutions are specifically contemplated hereby. While the use of such groups may dramatically effect the biological activity of the resulting compound, they do not significantly alter the ability to acylate a hydroxy group in the 17α position.

In addition, while the invention is generally described mainly in terms of steroid compounds having an exomethylene group in the 16th position, other functionally similar groups such as, for example, a cyclopropyl group or isobutyl group could also be disposed in position 16. Similarly, the B position could be substituted with any number of conventional groups including, for example, those found in corticosteroids.

The term "acylating compound" as used in accordance with the present invention includes, inter alia, anhydrides acyl halides and any other functionally equivalent compound which can be used to acylate the norprogesterones under the reaction conditions described herein. Anhydride compounds having between 1 and about 7 carbons in each anhydride chain are preferred. Anhydrides include acetic anhydride, propionyl anhydride, butyric anhydride pentanoic anhydride, hexanoic anhydride and heptanoic anhydride. The anhydrides may also be substituted or unsubstituted. For example, they may be halogen substituted, hydroxy substituted or branched. Acyl halides include acyl iodide, acyl bromide, acyl chloride or acyl fluoride. However, acyl chlorides are preferred. The term acyl halide is intended herein to mean compounds having between 1 and about 7 carbons in length. These include the halide forms of the anhydrides just discussed such as valeryl chloride. The acid halides may also be substituted or branched as previously described.

The acid catalyst in accordance with the present invention is perchloric acid.

As will be illustrated in the examples to follow, when a number of acids such as sulfuric acid, hydrochloric acid and trifluoro acetic acid were tried, substantially no acylated derivatives were realized. When p-toluenesulfonic acid ("TsOH") was used as a catalyst, several side products were formed which lowered yield and made extraction extremely difficult. It was surprising to find that only perchloric acid actually resulted in acceptable yields of the desired acyl derivatives without undesirable levels of side reactions. Table 1 illustrates the yields of acyl derivatives of the compound of Formula II using various acid catalysts.

TABLE 1

| Acid Catalase | Percent Yield | By-Products |
|---|---|---|
| $H_2SO_4$ | 4.23 | 3 |
| HCl | 10.45 | 1 |
| $CF_3COOH$ | 5.59 | 1 |
| TsOH | ~20–30 | 2 |
| $HClO_4$ | ~60–80 | |
| $H_3PO_4$ | 5.43 | 1 |

It was particularly surprising to discover that perchloric acid drove this reaction efficiently when the other acids listed above could not, without otherwise adversely effecting the steroid compound. In addition, achieving a 60 to 80% yield is, independently, quite an achievement in and of itself. However, doing so in a reaction mixture which can be run at room temperature, in a relatively short time, and with relatively little solvent, was particularly surprising.

In accordance with the process of the present invention, the norprogestin compound is reacted with at least one acylating compound in the presence of a perchloric acid catalyst so as to form a reaction mixture containing the corresponding acyl derivative. The amount of acylating compound used should be at least about a stoichiometric amount relative to the amount of the steroid compound to be acylated. However, in certain instances, less than a stoichiometric amount may be used. In more preferred embodiments, a stoichiometric excess of the acylating compound relative to the amount of the steroid compound is used. Generally, the amount of acylating agents should be provided in an amount of between about 1 and about 1.2 times the stoichiometric amount of the steroid compound.

The perchloric acid catalyst should be provided in an amount of between about 0.1 and about 5 times the stoichiometric amount of the norprogestin compound.

The reaction can be run in a solvent. Solvents may include methylene chloride, benzene, toluene, chloroform, ether and mixtures thereof. Other conventional solvents may also be used. It is also possible to practice the present invention in a solventless system using the anhydride or acyl halide as the solvent. When solvents are used and/or, when anhydrides or acyl halides are used in place of the solvent, the amount of said material should be sufficient to dissolve all of the norprogesterone compound being converted. Generally, however, no more than about twice the volume of the reactants are necessary. When solvents such as benzene or toluene are used, it may be necessary to reflux the reaction under heat. When methylene chloride is used, however, the reaction can be run in a hood at ambient room temperature, generally between about 60° and about 85° F. While the reaction is exothermic no step need be taken to heat or cool it. Thus, while the reaction mixture may be at an elevated temperature, the reaction environment need not be.

When conducting the reaction, the norprogesterone is dissolved in a solvent such as, for example, methylene chloride. The acylating compound and acid catalyst are then added. Often, the reaction produces a significant color change after between 30 minutes and about 2 hours. Once the reaction is complete, the neutralization and extraction process begins. Neutralization can begin by pouring the reaction mixture over ice water. This will react any residual acid halide or anhydride such that the corresponding acids are formed. Then, the acyl derivative of the steroid compound can be extracted from the reaction mixture by extraction with further solvent, such as, for example, methylene chloride. The amount of solvent used to extract the mixture generally ranges from between about 1 to about 5 times the volume of the diluted reaction mixture. Thereafter, the extracted reaction mixture is washed until a neutral pH is achieved.

The washing liquid used in the washing step can be any washing liquid conventionally used for such purposes including, without limitation, water, solutions of sodium bicarbonate including, for example, a saturated solution thereof, 5% NaOH or other inorganic base.

Finally, after washing, the acyl derivatives of the steroid compounds separated from the reaction mixture can be dried. Drying can be undertaken by use of a common desiccant such as sodium sulfate and the like. The resulting material can also be recrystalized by methods known in the art such as for example, recrystalization in ethyl acetate.

EXAMPLES

The following examples are meant for illustrative purposes only.

Example 1

135 milligrams of 16-methylene-17α-hydroxy-19-norprogesterone having the Formula (II) (Compound 1, R=H) were dissolved in 5 mL of methylene chloride. 0.4 mL propionyl anhydride and four drops (about 50 microliters) of 60% perchloric acid were added as catalysts to the norprogesterone solution. The reaction was conducted at room temperature. The color of the reaction mixture turned from yellow to dark red after 1½ hours. The reaction mixture was then poured into ice water in an amount of about 2 times the volume of the reaction mixture, extracted with methylene chloride in an amount of about 2 to 3 times the volume of the reaction mixture and washed with a saturated sodium bicarbonate solution followed by a subsequent washing with water until a neutral pH was reached. The extract was dried over sodium sulfate. The solvent was evaporated to yield a yellow oily compound. White crystals were obtained after chromatography by silica gel and recrystalization in ethyl acetate. 123 milligrams or approximately a 78% yield of 16-methylene-17α-hydroxy-19-norprogesterone propionate was recovered. mp 151°–152° C.; IR(KBr)2900,1750,1700,1600cm$^{-1}$;$^1$H NMR(CDCl$_3$) 5.86(4—H);5.6, 5.45(CH$_2$=);2.34(—COCH$_2$—);2.15(—COCH$_3$);0.76(18—CH$_3$); Calcd:C 75.00,H 8.33 Found: C 74.61,H 8.33.

Example 2

Crude 16-methylene-17α-hydroxy-19-norprogesterone butyrate was synthesized by the same method described in Example 1. 200 mg of crude 16-methylene-17α-hydroxy-19-norprogesterone (Compound 1) was dissolved in about 5 mL of methylene chloride. 0.4 mL butyric anhydride and 50 mL of perchloric acid were added thereto. The reaction was conducted at room temperature for 2 hours. White crystals were obtained after recrystalization in ethyl acetate. The result was 16-methylene-17α-hydroxy-19-norprogesterone butyrate in the yield of approximately 72%. mp 143°–144° C. IR(KBr)2900,1750,1650,1600cm$^{-1}$; $^1$HNMR (CDCl$_3$) 5.85(4—H),5.58,5.44(CH$_2$=);2.30(—COCH$_2$—);2.15 (—COCH$_3$);1.61(—CH$_2$—CH$_3$);0.95(CH$_3$—);0.75(18—CH$_3$).Calcd:C 75.38,H 8.54 Found:C 75.51,H 8.84.

Example 3

See generally Example 1. 100 milligrams of 16-methylene-17α-hydroxy-19-norprogesterone (Compound 1) was dissolved in 5 mL of methylene chloride. 0.4 mL of valeryl chloride and 4 drops of 60% perchloric acid were added. After thirty minutes, the reaction mixture turned dark red and TLC showed that the starting material had disappeared. The mixture was poured into ice water, extracted with methylene chloride, washed with a saturated solution of sodium bicarbonate and water until washing became neutral as previously described. The organic layer was dried over sodium sulfate and the solvents were removed to yield a yellow oil. After recrystalization in methanol, 76 milligrams of a pale yellow crystal of 16-methylene-17α-hydroxy-19norprogesterone valerate was realized equaling a 58.2% yield. mp 130–131 (MeOH) ;IR(KBr)2900,1750,1700,1650,1600cm$^{-1}$; $^1$HNMR(CDCl$_3$) 5.90(4—H),5.70, 5.54 (CH$_2$=)2.20(s.—COCH$_3$), 1.90 (tri.—COCH$_2$—), 1.10(m)CH$_3$—CH$_2$—CH$_2$—), 0.90(t, CH$_3$CH$_2$), 0.72(18—CH$_2$) . Calcd:C 74.30,H 8.88 (C$_{25}$CH$_{34}$O$_4$ ½MeOH) Found: 74.71,H 8.91.

Example 4

16-methylene-17α-hydroxy-19norprogesterone hexanoate was synthesized by the same method used in Example 1 using 200 mg amount of 16-methylene-17α-hydroxy-19norprogesterone (Compound 1) dissolved in 5 mL of methylene chloride. 0.4 mL of hexanoic anhydride was used as the acylating agent and 50 μL amount of 60% perchloric acid was used as the catalyst. After crystallization in ethyl acetate, pale yellow crystals were obtained. The yield was 72%. mp 131°–132° C. IR(KBr)2900,1745,1690, 1560cm$^{-1}$; $^1$HMNR (CDCl$_3$) 5.86 (4—H),5.58,5.42(CH$_2$=) ,2.3(t,—COCH$_2$—CH$_2$—), 2.11(—COCH$_3$),1.3(m,—CH$_2$—CH$_2$—CH$_2$—),0.88(t,—CH$_2$CH$_3$), 0.75(18—CH$_3$) .Calcd:C 76.06,H 8.92-Found: C75.67,H 9.19.

Example 5

16-methylene-17α-hydroxy-19-norprogesterone can be produced directly from NESTORONE™ (16-methylene-17α-acetoxy-19-norprogesterone or 16-methylene-17α-hydroxy-19-norprogesterone acetate). 90 milligrams of NESTORONE™ was dissolved in 5 mL of methanol. Four milliliters of 1N KOH were added, and stirred for one hour. The reaction mixture was poured into 50 mL of ice water. The precipitate was collected, washed with water until is was neutral, and dried over phosphorous pentoxide to yield 65 milligrams, 81.5% yield. The product was recrystalized with methanol to yield a white crystal having a melting point of 218°–219° C.

Example 6

The following procedure was used to generate the results illustrated in Table 1. 100 milligrams of 17α-hydroxy-16-methylene-19-norprogesterone (Compound 1) were dissolved in two milliliters of methylene chloride, 100 microliters of acid anhydride and 50 microliters of catalyst acid were added while stirring at room temperature. The reaction was traced by thin-layer-chromatography. Since, after two hours, some of the starting materials remained substantially unaltered, the reaction was allowed to continue overnight. (Approximately 15 hours total). The reaction mixture was poured into 2–4 times its volume of ice water and the organic layer was separated. The water phase was extracted with methylene chloride in an amount of between 2 and 3 times the volume (3 milliliters each). The combined organic phase was washed with saturated sodium bicarbonate followed by water until the washing became neutral. The organic phase was dried over sodium sulfate. The solvent was evaporated and the product was redissolved with 2–4 milliliters of methanol. 20 microliters of methanol solution was taken to measure the yield using a Perkin-Elmer HPLC system. For each instance, propionic anhydride was used as the acylation agent.

Example 7

17α-acetoxy-16-methylene-19-norprogesterone (NESTORONE™) was synthesized. 40 milligrams of 17α-hydroxy-16-methylene-19-norprogesterone (Compound 1) was dissolved in 200 μL of acetic acid, 20 μL of perchloric acid (60%) and 200 μL of acetic anhydride was added to the reaction mixture and stirred at room temperature for 30 minutes. The reaction mixture was poured into 4 mL of ice water, the white precipitate was collected by filtration. The crude product was crystallized in ethyl acetate, yield 70%, mp 176°–178° C.

The principles, preferred embodiments and modes of operation of the present invention have been described in the foregoing specification. The invention which is intended to be protected herein, however, is not to be construed as limited to the particular embodiments disclosed, since these are to be regarded as illustrative rather than restrictive. Variations and changes may be made by others without departing from the spirit and scope of the invention.

I claim:

1. A method of synthesizing acylated derivative of norprogesterone compounds comprising the steps of:

providing a norprogesterone compound having the tetracyclic ring system of asteroid substituted in the 16th position with an exomethylene group and having a hydroxyl group in the 17α position;

and reacting said norprogesterone compound with at least one acylating agent in the presence of perchloric acid, so as to form a reaction mixture containing the corresponding ester derivative of said norprogesterone compound.

2. The compound produced by the method of claim 1.

3. The method of claim 1 wherein said norprogesterone compound provided is a 16-methylene-17α-hydroxy-19-norpregn-4-ene-3,20-dione.

4. The compound produced by the method of claim 3.

5. The method of claim 1 wherein said acylating compound is provided in at least about a stoichiometric amount relative to the amount of said norprogesterone compound.

6. The method of claim 5 wherein said acylating compound is provided in an amount in excess of a stoichiometric amount relative to the amount of said norprogesterone compound.

7. The method of claim 6 wherein said acylating compound is provided in an amount of between about 1 and about 1.2 times the stoichiometric amount said norprogesterone compound.

8. The method of claim 1 wherein said reaction is run in a solvent.

9. The method of claim 8 wherein said solvent is selected from the group consisting of methylene chloride, benzene, toluene, chloroform, and ether.

10. The method of claim 1 wherein said perchloric acid is provided in between about 0.1 and about 5 times the stoichiometric amount of said norprogesterone compound.

11. The method of claim 1 wherein said acylating compound is selected from the group consisting of anhydrides, and acyl halides.

12. The method of claim 1 wherein said reacting step is conducted at room temperature of between about 60° F. and about 85° F.

13. The method of claim 1 further comprising the step of extracting said acyl derivative of said norprogesterone compound from said reaction mixture.

14. The method of claim 13 further comprising the step of washing said acyl derivative of said norprogesterone compound.

15. The method of claim 14 further comprising the step of drying the washed and extracted reaction product.

16. A method of synthesizing acylated derivatives of 16-methylene-17α-hydroxy-19-norpregn-4-ene-3,20-dione comprising the steps of:

providing , a 16-methylene-17α-hydroxy-19-norpregn-4-ene-3,20-dione; and reacting said 16-methylene-17α-hydroxy-19-norpregn-4-ene-3,20-dione with at least a stoichiometric amount of at least one acylating compound selected from the group consisting an anhydride and an acyl halide in the presence of perchloric acid at room temperature so as to form the corresponding acyl derivative thereof.

17. The compound produced by the method of claim 16.

18. The method of claim 16 wherein said acylating compound is an anhydride of acids of having between about 1 and about 7 carbons in length.

19. The method of claim 18 wherein said acylating compound is selective from the group consisting of acetic anhydride, propionyl anhydride, butyric anhydride, pentanoic anhydride, hexanoic anhydride and heptanoic anhydride.

20. The compound produced by the method of claim 19.

21. The method of claim 16 wherein said acylating compound is an acyl halide having between about 1 and about 7 carbons in length.

22. The method of claim 21 wherein said acyl halide is an acyl chloride.

* * * * *

UNITED STATES PATENT AND TRADEMARK OFFICE
CERTIFICATE OF CORRECTION

PATENT NO. : 5,710,293

DATED : January 20, 1998

INVENTOR(S) : Li

It is certified that error appears in the above-identified patent and that said Letters Patent is hereby corrected as shown below:

Column 2, line 32, "asteroid" should read --a steroid--.

Column 2, line 65, "asteroid" should read --a steroid--.

Column 6, line 62, "0.72(18-$CH_2$)" should read --0.72(18-$CH_3$)--.

Column 8, line 9, "asteroid" should read --a steroid--.

Signed and Sealed this

Fifth Day of May, 1998

BRUCE LEHMAN

*Attest:*

*Attesting Officer*      *Commissioner of Patents and Trademarks*